United States Patent [19]

Farrar

[11] Patent Number: 4,543,422

[45] Date of Patent: Sep. 24, 1985

[54] SYNTHESIS OF VINYL ESTERS

[75] Inventor: David Farrar, West Yorkshire, England

[73] Assignee: Allied Colloids Limited, England

[21] Appl. No.: 543,734

[22] Filed: Oct. 20, 1983

[30] Foreign Application Priority Data

Oct. 26, 1982 [GB] United Kingdom ................. 8230580

[51] Int. Cl.$^4$ ............................................. C07C 67/02
[52] U.S. Cl. .................................................... 560/217
[58] Field of Search ........................................ 560/217

[56] References Cited

U.S. PATENT DOCUMENTS 2,822,348 2/1958 Haslam ................................. 560/217
3,293,283 12/1966 Dobson et al. ...................... 560/217

OTHER PUBLICATIONS

Kaiser, Emil et al., J. Am. Chemical Society, vol. 78 (1956) pp. 3841–3843.
Kirk–Othmer Encyclopedia of Chemical Technology, 2nd Ed. (1966), vol. 8, pp. 356–359.
Saiga, Daini et al., Chemical Abstracts vol. 83 (1975) #59,775y.
Hamamoto, Yoshito et al., Chemical Abstracts vol. 84, (1976), #136,275f.

Primary Examiner—Natalie Trousof
Assistant Examiner—L. Hendriksen
Attorney, Agent, or Firm—Lawrence Rosen

[57] ABSTRACT

A vinyl ester of the formula $R^3COOR^4$ where $R^3$ is $CH_2=CH-$ or $CH_2=C.CH_3-$ and $R^4$ contains at least four carbon atoms and is selected from alkyl, cycloalkyl and aminoalkyl is conducted by reaction of an ester $R^3COOR^1$, where $R^1$ is $C_{1-3}$ alkyl, with metal alcoholate formed from an alcohol $R^4OH$ and titanium, aluminum, zirconium, calcium or magnesium in the absence of water or reactive alcohol.

13 Claims, No Drawings

SYNTHESIS OF VINYL ESTERS

It is known to be able to make esters of carboxylic acids by an ester interchange reaction according to the reaction scheme $$RCOOR^1 + R^2OH \rightleftharpoons RCOOR^2 + R^1OH$$

In this typically R is an aliphatic or aromatic group, $R^1$ is a methyl or ethyl group and $R^2$ is an aliphatic group containing more carbon atoms than $R^1$. A catalyst is generally used in order to promote the desired exchange reaction. Various metal alcoholates have been proposed for use as the catalyst. It is however also known to provide the alcohol $R^2OH$ for the reaction in the form of a metal alcoholate instead of using alcohol and catalyst. Thus in JACS 78, page 3841 Kaiser et al describe, for example, the reaction of tosylglycine methyl ester with aluminium isopropoxide to form aluminium methoxide and tosylglycine isopropyl ester.

It is recognised that it is difficult to achieve a good conversion in this reaction and Kaiser et al describe ways of improving the conversion. In one method they conduct the reaction in the presence of a solvent for the starting aluminium alcoholate and in practice they use alcohol as this solvent. In another process they add the alcohol of the starting aluminium alcoholate (e.g. isopropanol) to the reaction mixture in order to convert the aluminium alcoholate formed during the reaction (e.g. aluminium methoxide) back to aluminium isopropoxide in the reaction mixture.

Particular problems arise in ester interchange reactions that are conducted starting from a vinyl ester such as methyl acrylate or methyl methacrylate. Although ester interchange does occur, in most processes it is accompanied by the formation of undesirable by-products, due especially to addition across the double bond of the vinyl group. Much research has therefore been conducted into developing processes that give a minimum of condensation across the double bond and a maximum of ester interchange. The problem is particularly acute in the synthesis of dialkylaminoalkyl acrylates and methacrylates starting from acrylic or methacrylic lower alkyl ester and a dialkylamino alcohol. The end products are very valuable, for instance for the formation of cationic polymers, and ester interchange is generally the preferred synthesis since starting from, for instance, acrylic acid or acryloyl chloride incurs various disadvantages.

In U.S. Pat. No. 2,138,763 various amino alcohols are reacted with methyl methacrylate in the presence of an alkali metal alcoholate ester interchange catalyst, generally a small amount of sodium methoxide. In Examples 6 and 7 methacryloylchloride is reacted with the sodium alcoholate of the chosen amino alcohol. However, the use of methacryloylchloride is unsatisfactory on a commercial scale, for instance because of difficulties of handling it.

In Japanese Application No. 71748/73 (Kokai No. 7519716) it is proposed to conduct the ester interchange between an amino alcohol and methyl or ethyl acrylate or methacrylate in the presence of a catalytic amount of a magnesium alcoholate, generally formed from the starting alcohol. It is emphasised that the amount of catalyst should be not more than 10% and the amount used in the examples is 3%. Other processes that have been described include, for example, Japanese Kokai No. 75142513, in which a calcium compound is used as catalyst, U.S. Pat. No. 4,059,617 in which a phenoxide is used as a catalyst, Japanese Kokai No. 77153991 in which a lithium or a sodium compound is used as catalyst, and British Pat. Nos. 1 572 438 and 1 556 310 in which tin compounds are used as catalysts. Although the use of a metal alcoholate as a reactant rather than as a catalyst is known for the production of other esters (see the article by Kaiser et al), generally in the presence of free alcohol, this process has never been proposed in the context of vinyl esters presumably because of the known probability of poor yields or undesirable side reactions.

It has become accepted that the best way of effecting ester interchange for vinyl esters is by reaction of the vinyl lower alkyl ester with the chosen alcohol in the presence of a catalyst. The catalyst is generally a titanium alcoholate or aluminium alcoholate but, as is apparent from the literature quoted above, there have been numerous proposals to use sodium or other alcoholates. Although these processes are used widely they are not entirely satisfactory. It is difficult to obtain good yields of pure products and in particular formation of undesirable byproducts is difficult to avoid. The process involves the formation of azeotropes between alcohol and ester and it is difficult to separate these azeotropes into their components.

We have now surprisingly found that it is possible to achieve high yields of pure product, in the substantial absence of impurities, by reaction of a vinyl lower alkyl ester with an appropriate metal alcoholate provided the metal is selected from a narrow group of metals and provided the reaction is conducted in the substantial absence of any water or reactive alcohol.

In particular in the invention we make an ester of the formula $R^3COOR^4$ where $R^3$ is $CH_2=CH-$ or $CH_2=C(CH_3)-$ and $R^4$ contains at least four carbon atoms and is selected from alkyl, cycloalkyl and aminoalkyl by reaction of a compound of the formula $R^3COOR^1$, where $R^1$ is $C_{1-3}$ alkyl, in the presence of a metal alcoholate formed from an alcohol $R^4OH$ and in this process the metal alcoholate provides the groups $R^4$ that are utilised in forming the desired ester and reacts with the compound $R^3COOR^1$, the reaction is conducted in the substantial absence of water or reactive alcohol and metal is selected from titanium, aluminium, zirconium, calcium and magnesium.

An important feature of the invention relates to the use of this process for forming aminoalkyl esters, since the difficulties of ester interchange are particularly serious with these and the process of the invention is especially effective for the formation of such esters. The alkyl group of the aminoalkyl radical generally contains at least two carbon atoms and the aminoalkyl group is generally a dialkyl aminoalkyl group. Preferably it is a group of the formula $(R^5)_2N-C_nH_{2n}$, where n is two or three and the groups $R^5$, which may be the same or different, are $C_{1-3}$ alkyl. The process is of particular value when the aminoalkyl group is dimethylaminoethyl. The metal may be zirconium but is often titanium, aluminium, calcium or magnesium and, as discussed below, best results are generally achieved with calcium of magnesium.

The aminoalkyl esters are known compounds and are useful for forming known polymers that are of value as, for instance, flocculants. The process is, however, also applicable to the production of alkyl and cycloalkyl esters having more than four, and generally more than five, carbon atoms. Cycloalkyl esters generally contain five to eight carbon atoms. Preferably, however, the esters are alkyl esters containing from five to thirty carbon atoms. The long chain esters, for instance containing fifteen to thirty carbon atoms and preferably twenty to twenty four, typically around twenty two carbon atoms are of particular value in the production of polymers for use as suspension stabilisers while the cycloalkyl and shorter chain length alkyl esters, for instance containing six to fifteen and generally seven to ten, typically around eight, carbon atoms, are of value as pour point depressants. They are all known compounds.

It has normally been assumed, in ester interchange reactions, to be desirable to have any metal alcoholate in solution in the reaction mixture, i.e. the mixture should be homogeneous. An important feature of the invention is that we have found that in the particular ester interchange process of the invention it is often very advantageous that the starting metal alcoholate should be insoluble in the reaction mixture. The reaction is generally conducted in the absence of any solvent and so whether or not the alcoholate is soluble in the mixture will depend on the metal, the alcohol used for forming the alcoholate, and the starting ester. In practice, the alcoholates of calcium and magnesium are generally insoluble and particularly good results are achieved when $R^4$ represents aminoalkyl, as discussed above, and the metal is selected from calcium and magnesium. By saying that the alcoholate is insoluble we mean that its solubility is so low that the great majority is insoluble, for instance, its solubility is below 5% and generally below 1% in the reaction mixture.

An important feature of the invention is that, as a result of utilising defined materials in the absence of free alcohol, it is possible to operate the process commercially in a particularly effective manner so as to obtain maximum yields with minimum consumption of reactants. An important feature of preferred processes of the invention is that the metal alcoholate formed in the reaction should be removed from the reaction mixture and should then be reacted with excess alcohol $R^4OH$ and the resultant metal alcoholate is then recycled to the reaction mixture. Thus this reaction with alcohol $R^4OH$ must occur in the substantial absence of the ester $R^3COOR^1$ and so, by this process, one achieves not only substantially total reuse of the metal but also avoids the formation of azeotropes between the starting ester and the alcohol.

The preferred process of the invention involves carrying out the following sequential steps. In step A the ester interchange reaction is conducted between the metal alcoholate formed from the alcohol $R^4OH$ and an excess of the ester $R^3COOR^1$ to form a mixture containing the ester $R^3COOR^4$, unreacted ester $R^3COOR^1$ and metal alcoholate that has at least partially been converted to an alcoholate formed from the alcohol $R^1OH$. In step B this alcoholate is separated from the reaction mixture, the ester $R^3COOR^4$ is recovered from the reaction mixture and the ester $R^3COOR^1$ is recycled for use in step A. In step C the separated alcoholate from step B is reacted, in the substantial absence of ester $R^3COOR^1$, with excess alcohol $R^4OH$ to form alcohol $R^1OH$ and alcoholate formed from the alcohol $R^4OH$. In step D this alcoholate, formed in step C, is separated and recycled for use in step A and the alcohol $R^4OH$ is recovered and recycled for use in step C. The alcohol $R^1OH$ is taken off as an end product.

Generally step B is effected by separating the alcoholate from the esters followed by separating the esters by fractional distillation, while step C is effected by separating the alcoholate from the alcohols followed by separating the alcohols by fractional distillation. When the alcoholate in a mixture is insoluble in that mixture separation can be by filtration (for instance centrifugation) but if the alcoholate is soluble separation can be by evaporation of the more volatile organic component from the less volatile metal alcoholate. In order to avoid prolonged heating this evaporation is preferably by flash evaporation.

The starting ester is generally methyl acrylate or methacrylate or ethyl acrylate or methacrylate. The starting metal alcoholate may be formed only from the alcohol $R^4OH$ in which event the metal alcoholate has the formula $M(OR^4)_m$ where M is the metal and m is the valency of the metal, but in some instances it is desirable for some, but not all, of the valencies of the metal M to be blocked by an inert group $R^6$ so that the metal alcoholate then has the formula $M(OR^4)_{m-n}(R^6)_n$ where n is a number less than m and is generally 1. $R^6$ is any group that is substantially less reactive in the ester interchange reaction than the group $OR^4$, with the result that it will remain attached to the metal M during the reaction. It is normally an alkyl or alkoxy group containing eight to thirty carbon atoms but, if it is an alkoxy group, it is generally essential for it to contain more carbon atoms than $R^4$ as otherwise it may enter into the reaction. A preferred blocking group $R^6$ is stearyl. The inclusion of a blocking group reduces the risk of the metal entering into unwanted side reactions and is generally of interest only when the metal is titanium. Another effective way of minimising the risk of unwanted side reactions when the metal is titanium is to use it as a blend with zirconium. Other blends of metals may also be used in the invention.

It is essential in the invention to use one or more of the named five metals since the use of alcoholates formed with other metals does not give satisfactory results. For instance the use of sodium or barium alcoholates leads to high byproduct formation, primarily due to addition across the double bond, while the use of other metal alcoholates leads to little or no reaction occurring. The desired alcoholate may be prepared by addition of the chosen metal to the chosen alcohol.

The reaction is preferably conducted using an excess of the starting ester, for example 1.0 to 10 moles of ester per mol of alcoholate. The reaction mixture should be free of the starting alcohol or of any other alcohol that could react under the prevailing process conditions, and is generally free of any alcohol. The reaction mixture should be substantially anhydrous. Very small amounts of water or alcohol may be tolerated but even these may lead to some by-product formation.

The reaction may be carried out simply by mixing the starting ester with the chosen alcoholate. With the preferred alcoholates, of calcium or magnesium, no heating is necessary and the reaction proceeds satisfactorily at ambient temperature, but in general temperatures between 10° and 50° C. can be used. With the titanium, zirconium and aluminium alcoholates the reaction may proceed at ambient temperatures but it is generally desirable to heat the mixture, for instance to reflux, often at temperatures of 70° to 95° C. The reaction is generally conducted under atmospheric pressure.

The reaction proceeds to an equilibrium position. The time required to reach this depends on the temperature but is generally 10 minutes to 3 hours. For instance calcium or magnesium alcoholates reacted at ambient temperatures may require 30 to 75 minutes, or less at higher temperatures, while aluminium or titanium alcoholates may require 1 to 2 hours at reflux. The equilibrium may be represented schematically by the equation:

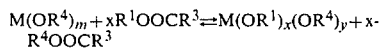

wherein $x+y=m$ and x and y are generally both above 0, usually above 0.1, preferably 0.5 to 2. For simplicity we have not shown in this reaction scheme the possibility of the use of blocking groups $R^6$, but of course they can be present as well.

The reaction is generally allowed to proceed substantially to the equilibrium position although it is not essential to attain final equilibrium. The desired ester may be recovered from the reaction mix continuously during the reaction or at any time during the reaction or the reaction may be conducted batch wise with the ester being separated at the end of each batch. The desired ester may be recovered in any convenient way, for example by distillation or by centrifugation or other filtration method of removing solid alcoholate, but preferably is removed as part of the cyclic process described above. The alcoholate can be removed, for instance by filtration, either continuously or batchwise. The mixed alcoholates recovered from the reaction mixture will often contain approximately one third to one half of the initial amount of alcohol $R^4OH$ (introduced as alcoholate) and it is therefore desirable to reuse this aminoalcohol. For this purpose the mixture of alcoholates is converted back to the starting materials. This can be done by reaction of the mixed alcoholate with excess dialkylamino alcohol in accordance with the reaction scheme

Reactant regenerated in this way has proved as effective as material prepared initially from the alcohol $R^4OH$ and the chosen metal.

The following are some examples. Example 1 is an example of a conventional catalytic process such as is conventionally used commercially. Example 2 describes the preparation of a starting alcoholate for use in the invention. Examples 3 to 8 and 10 are examples of the invention and Example 9 is comparative.

EXAMPLE 1

2.5 moles of methyl acrylate and 1.5 moles of DMAE (dimethylamino ethanol) were charged into a reaction vessel. Ti(DMAE)$_4$ to 11.4% by weight of the alcohol was added as catalyst. The mixture was heated to boiling point and methanol/methyl acrylate azeotrope was removed. The pot temperature was initially 89° C. and increased to 166° C. on reaction completion. The percentage of high-boilers (by-products) based on DMAEA was determined as the reaction proceeded. After 200 minutes and 66.5% conversion of DMAE to DMAEA, the percentage was 2.2% (by weight), while after 350 minutes and almost complete conversion the percentage was 8.2%.

EXAMPLE 2

Turnings of magnesium were added in portions to at least one mole excess of dimethylamino ethanol at 130° C. A crystal of iodine is useful in starting the reaction. Heating was continued until most of the metal had reacted (this may take several days). The mixture was then cooled and the dimethylamino ethanol decanted off. The precipitate was then stripped under 10 mm Hg vacuum in an oil bath at 140° C. until no more dimethylamino ethanol could be removed. The other alcoholates used in the examples were made in similar manner or by conversion of lower alkyl alcoholates of the chosen metal.

EXAMPLE 3

Calcium or magnesium alcoholate prepared as in Example 2 was placed in a flask. Methyl acrylate was added to give a mole ratio of 5 moles of acrylate to 1.5 moles of metal alcoholate. A heterogeneous mixture was formed since the methyl acrylate did not dissolve the solid alcoholate. Solubility tests at room temperature showed that the calcium alcoholate dissolved in an amount less than 0.1% in the reaction mixture and the magnesium alcoholate dissolved in an amount of less than 0.6%.

The reaction proceeded at 25° C. and the amount of dimethylamino ethyl acrylate (DMAEA), expressed as a molar percentage based on the amount of alcohol in the alcoholate introduced into the reaction vessel, was determined at various times during the reaction. After 60 minutes the mixture was centrifuged to remove the solid alcoholates and the liquid phase fractionally distilled to remove the methyl acrylate. The residue, of DMAEA, was analysed and was found to be free of high boiling or other by-products. The results are given in Table 1. Reaction beyond 60 minutes was found, in other experiments, to give no significant change in conversion.

TABLE 1

| Reaction time (mins) | % DMAEA Mg alcoholate | % DMAEA Ca alcoholate |
| --- | --- | --- |
| 10 | 12.5 | 10.0 |
| 20 | 17.0 | 15.5 |
| 30 | 19.5 | 18.0 |
| 40 | 21.6 | 19.5 |
| 60 | 24.6 | 20.5 |

EXAMPLE 4

The process of Example 3 was repeated, with heating, using aluminium or titanium alcoholate instead of calcium or magnesium alcoholate substantially.

When the temperature was at reflux (at about 85° C.) reaction started and continued to equilibrium as the reflux temperature rose to 92° C. over a total period of 1.5 hours. Reaction beyond this time gave no significant change in conversion. The results of GLC analysis for DMAEA are shown in Table 2.

TABLE 2

| Reaction time (mins) | % DMAEA Al alcoholate | % DMAEA Ti alcoholate |
| --- | --- | --- |
| 10 | 4.7 | 27.4 |
| 20 | 10.0 | 29.7 |
| 30 | 16.5 | 30.5 |
| 35 | 25.5 | 30.7 |
| 60 | 28.0 | 30.8 |
| 90 | 28.7 | 30.8 |

EXAMPLE 5

Methyl methacrylate (1 mole) was reacted with the Mg or Ca alcoholates of dimethylamino ethanol (0.3 moles) at 25° C. The amount of dimethylamino ethylmethacrylate (DMAEMA) formed at various times during the reaction was determined and the results are given in Table 3. When the reaction mixtures were allowed to stand, no high boiling impurities were apparent after 24 hours at room temperature in either reaction mixture and there was no significant change in conversion after 60 Minutes.

TABLE 3

| Reaction time (mins) | % DMAEMA Mg alcoholate | Ca alcoholate |
| --- | --- | --- |
| 10 | 5.8 | 8.0 |
| 20 | 11.1 | 14.3 |
| 35 | 16.1 | 15.9 |
| 45 | 18.4 | 18.4 |
| 60 | 21.8 | 21.8 |

EXAMPLE 6

62.5 g of zirconium tetra dimethylamino ethoxide and 187.5 g of titanium tetra dimethylamino ethoxide were mixed with 349.7 g methyl acrylate and 0.6 g phenothiazine to give a 5:3 molar methyl acrylate to dimethylaminoethanol ratio.

The resultant mass was heated to a temperature such that the methyl acrylate reached reflux temperature. After sixty minutes the reaction had reached equilibrium giving 23.6% DMAEA. The volatile components were removed by flash evaporation and the resultant liquid was analysed as $Zr_{0.231}Ti_{0.769}(OMe)_{1.65}(DMAE)_{2.35}$. $OMe=OCH_3$: $ODMAE=OCH_2CH_2N(CH_3)_2$.

EXAMPLE 7

443 g zirconium tetra dimethylamino ethoxide and 103.2 g methyl acrylate were mixed together and 0.1 g phenothiazine added. The resultant mix was then heated with stirring till the methyl acrylate reached reflux temperature. After 40 minutes the reaction contained 20.0% by weight DMAEA.

EXAMPLE 8

5 mole equivalents of methyl acrylate were reacted with 1 mole equivalent $Ti(DMAE)_4$ at 80° C. Once reaction equilibrium was attained, after 60 minutes, the volatiles were removed by rapid distillation at 120° C. and 20 mm Hg pressure and DMAEA was separated. Some equilibrium reversal occurred due to slight fractionation under these conditions. The resultant titanium alkoxide was regenerated by the addition of 1–2 moles dimethylaminoethanol per mole of methoxide ligand. Methanol and DMAE were removed slowly by distillation on a rotary evaporator and the residue was recycled for use in the main reaction. The process was repeated 15 times. Table 4 gives the time to equilibrium in each main reaction and the analysis of the titanium alkoxide that had been made in the previous cycle and that had been converted for use in that main reaction

TABLE 4

| Recycle | $Ti(OCH_3)_x(ODMAE)_{4-x}$ x = | Time to equilibrium (minutes) |
| --- | --- | --- |
| 1 | 1.71 | 70 |
| 2 | 1.49 | 70 |
| 3 | 1.53 | 70 |
| 4 | 1.44 | 60 |
| 5 | 1.39 | 80 |
| 6 | 1.32 | 60 |
| 7 | 1.51 | 60 |
| 8 | 1.46 | 60 |
| 9 | 1.60 | 40 |
| 10 | 1.32 | 40 |
| 11 | 1.62 | 60 |
| 12 | 1.43 | 40 |
| 13 | 1.66 | 60 |
| 14 | 1.36 | 50 |
| 15 | 1.47 | 60 |

It will be seen that the recycled alkoxide maintains its effectiveness.

EXAMPLE 9

When the process of Example 3 was attempted using the corresponding sodium alcoholate reaction occurred exothermically and resulted in very high levels of by-products being formed whether the reactor was cooled or not. Similar results were obtained when the sodium alcoholate was replaced with potassium, lithium or barium alcoholates.

EXAMPLE 10

1170 g titanium tetra isopropanate and 2142 g 2-ethyl hexanol were heated together in a stirred reactor equipped with a fractionation column and reflux splitter. Isopropanol was removed at the top of the column and the pot temperature progressively increased to 160° C. at which point vacuum was progressively applied to remove the last traces of the isopropanol. 930 g isopropanol (94% theory) was recovered although there was some loss down the vacuum line. 14 g 2-ethyl hexanol was removed from the column bottom once the vacuum was released. The reactor contained 2283 g tetra (2-ethyl hexyl) titanate in the form of a mobile amber liquid with no sign of precipitate.

The metal alcoholate was then stripped on a rotaryexporator at 140° C. and 10 mm Hg pressure to remove any residual volatiles.

423 g (5 moles) methyl acrylate and 423 g (0.75 moles) of the tetra (2-ethyl hexyl) titanate (as prepared above) were charged into a glass reactor equipped with stirrer and reflux condenser. The reaction mass was heated until the methyl acrylate reached reflux temperature. The extent of reaction was followed by GLC analysis. The reaction mass contained 27.2% w/w 2-ethyl hexyl acrylate after 5 minutes and 47.6% after 15 minutes. Reaction for a further 45 minutes showed no further increase in product and did not lead to formation of impurities.

I claim:

1. A process for making an ester of the formula $R^3COOR^4$, where $R^3$ is $CH_2=CH-$ or $CH_2=CCH_3-$ and $R^4$ contains at least four carbon atoms and is selected from alkyl, cycloalkyl and aminoalkyl, by reaction from a compound formula $R^3COOR^1$, where $R^1$ is $C_{1-3}$ alkyl, in the presence of metal alcoholate formed from an alcohol $R^4OH$, and in which the metal alcoholate provides the groups $R^4$ utilized in forming the ester and reacts with the compound $R^3COOR^1$, the reaction is conducted in the substantial absence of water or reactive alcohol and the metal is selected from titanium, aluminum, zirconium, calcium and magnesium; and wherein the metal alcoholate formed in the reaction is removed from the resulting reaction product mixture and reacted with excess alcohol $R^4OH$, in the substantial absence of compound $R^3COOR^1$, the metal alcoholate thus formed is recycled to the reaction.

2. A process according to claim 1, in which $R^4$ is aminoalkyl and the metal is selected from titanium, aluminium, calcium, magnesium.

3. A process according to claim 1, in which $R^4$ is $(R^5)_2N$—$C_nH_{2n}$, where $R^5$, which may be the same or different, are $C_{1-3}$ alkyl and n is 2 or 3.

4. A process according to claim 1, in which the metal is selected from calcium and magnesium and the alkylate formed from the alcohol $R^4OH$ is insoluble in the reaction mixture and $R^4$ is $(R^5)_2N$—$C_nH_{2n}$, where $R^5$, which may be the same or different, are $C_{1-3}$ alkyl and n is 2 or 3.

5. A process according to claim 1, in which the alcoholate formed from the alcohol $R^4OH$ is insoluble in the reaction mixture.

6. A process according to claim 1, in which the metal alcoholate formed from the alcohol has the formula $M(OR^4)_m$ where M is the metal and m is the valency of the metal and the metal alcoholate formed in the reaction has the formula $M(OR^1)_x(OR^4)_y$ where $x+y=m$ and x and y are each numbers above 0.1 and below m.

7. A process according to claim 1, in which the reaction is conducted in the absence of solvent using 1.0 to 10 moles of ester $R^3COOR^1$ per mole alcoholate at a temperature of 10° to 50° C. when the metal is calcium or magnesium or at least 70° C. when the metal is zirconium, titanium or aluminium.

8. A process according to claim 1 in which the reaction is carried out in the presence of an excess amount of the compound $R^3COOR^1$.

9. A process according to claim 1, in which the reaction is carried out in the absence of solvent.

10. A process for making an ester of the formula $R^3COOR^4$, where $R^3$ is $CH_2$=CH— or $CH_2$=$CCH_3$— and $R^4$ contains at least four carbon atoms and is selected from alkyl, cycloalkyl and aminoalkyl, by reaction from a compound formula $R^3COOR^1$, where $R^1$ is $C_{1-3}$ alkyl, in the presence of metal alcoholate formed from an alcohol $R^4OH$, and in which the metal alcoholate provides the groups $R^4$ utilised in forming the ester and reacts with the compound $R^3COOR^1$, the reaction is conducted in the substantial absence of water or reactive alcohol and the metal is selected from titanium, aluminium, zirconium, calcium and magnesium, and the reaction is carried out in the sequential steps:

(A) the reaction is conducted between (a) the metal alcoholate formed from the alcohol $R^4OH$ and (b) an excess of the ester $R^3COOR^1$, to form a mixture containing the ester $R^3COOR^4$, unreacted ester $R^3COOR^1$ and metal alcoholate that has at least partially been converted to an alcoholate formed from the alcohol $R^1OH$, (B) alcoholate is separated from the reaction mixture and the ester $R^3COOR^4$ is recovered from the reaction mixture and the ester $R^3COOR^1$ is recycled for use in step A, (C) the separated alcoholate is reacted, in the substantial absence of ester $R^3COOR^1$, with excess alcohol $R^4OH$ to give alcohol $R^1OH$ and alcoholate formed from the alcohol $R^4OH$, (D) this alcoholate is separated and recycled for use in step A, and alcohol $R^4OH$ is recovered and recycled for use in step C.

11. A process according to claim 10, in which step B is effected by separating the alcoholate from the esters and then separating the esters by fractional distillation and step C is effected by separating the alcoholate from the alcohols and then separating the alcohols by fractional distillation.

12. A process according to claim 10, in which the alcoholate obtained in step A is insoluble in the mixture and separation of the said alcoholate from the esters in step B is by filtration.

13. A process according to claim 10, in which the alcoholate obtained in step A is soluble in the mixture and separation of the said alcoholate is by evaporation of the esters.

* * * * *